(12) United States Patent
Khasnobish et al.

(10) Patent No.: US 11,395,642 B2
(45) Date of Patent: Jul. 26, 2022

(54) METHOD AND SYSTEM FOR NON-CONTACT BIO-SIGNAL DETECTION USING ULTRASOUND SIGNALS IN WHICH MAGNITUDE AND PHASE SIGNALS ARE OBTAINED FROM IN-PHASE AND QUADRATURE BASEBAND SIGNALS

(71) Applicant: Tata Consultancy Services Limited, Mumbai (IN)

(72) Inventors: Anwesha Khasnobish, Kolkata (IN); Raj Rakshit, Kolkata (IN); Arijit Sinharay, Kolkata (IN); Tapas Chakravarty, Kolkata (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 211 days.

(21) Appl. No.: 16/827,743

(22) Filed: Mar. 24, 2020

(65) Prior Publication Data

US 2021/0022713 A1 Jan. 28, 2021

(30) Foreign Application Priority Data

Jul. 26, 2019 (IN) .............................. 201921030330

(51) Int. Cl.
*A61B 8/08* (2006.01)
*A61B 8/02* (2006.01)
(Continued)

(52) U.S. Cl.
CPC .............. *A61B 8/5207* (2013.01); *A61B 8/02* (2013.01); *G01N 29/46* (2013.01);
(Continued)

(58) Field of Classification Search
CPC ..... A61B 8/5207; A61B 8/02; A61B 5/02444; A61B 5/0816; A61B 5/113; A61B 8/48;
(Continued)

(56) References Cited

U.S. PATENT DOCUMENTS 5,549,414 A 8/1996 Boxall et al.
10,172,592 B2 1/2019 Ward, III et al.
(Continued)

FOREIGN PATENT DOCUMENTS

EP 3441783 A1 2/2019

OTHER PUBLICATIONS

Scalise, Lorenzo. (2012). Non Contact Heart Monitoring. 10.5772/22937. https://www.researchgate.net/publication/221923114. (Year: 2012).*

(Continued)

*Primary Examiner* — Christopher Koharski
*Assistant Examiner* — Richmond J Van Winter
(74) *Attorney, Agent, or Firm* — Finnegan, Henderson, Farabow, Garrett & Dunner, LLP

(57) ABSTRACT

This disclosure relates generally to bio-signal detection, and more particularly to method and system for non-contact bio-signal detection using ultrasound signals. In an embodiment, the method includes acquiring an in-phase I(t) baseband signal and a quadrature Q(t) baseband signal associated with an ultrasound signal directed from the sensor assembly towards the target. Magnitude and phase signals are calculated from the in-phase and quadrature baseband signals, and are filtered by passing through a band pass filter associated with a predefined frequency range to obtain filtered magnitude and phase signals. Fast Fourier Transformation (FFT) of the filtered magnitude and phase signals is performed to identify frequency of dominant peaks of spectrum of the magnitude and phase signals in the ultrasound signal. Value of the bio-signal associated with the target is determined based on weighted values of the frequency of the dominant peaks of the magnitude and phase signals.

13 Claims, 7 Drawing Sheets

(51) Int. Cl.
  *G01N 29/46* (2006.01)
  *G01S 7/52* (2006.01)
  *G01S 15/89* (2006.01)

(52) U.S. Cl.
  CPC ...... *G01S 7/52028* (2013.01); *G01S 7/52085* (2013.01); *G01S 15/8977* (2013.01)

(58) Field of Classification Search
  CPC ... A61B 8/5223; A61B 8/4272; A61B 8/4444; G01N 29/46; G01S 7/52028; G01S 7/52085; G01S 15/8977
  See application file for complete search history.

(56) References Cited

U.S. PATENT DOCUMENTS

| | | | |
|---|---|---|---|
| 2009/0324040 A1* | 12/2009 | Lindop | G01S 15/8977 382/131 |
| 2010/0312106 A9 | 12/2010 | Blalock et al. | |
| 2011/0208060 A1* | 8/2011 | Haase | A61B 5/1135 600/453 |
| 2017/0300650 A1* | 10/2017 | Margon | A61B 5/002 |
| 2021/0275056 A1* | 9/2021 | McMahon | A61B 5/1126 |

OTHER PUBLICATIONS

Schrumpf, Fabian, Sturm, Matthias, Bausch, Gerold and Fuchs, Mirco. "Derivation of the respiratory rate from directly and indirectly measured respiratory signals using autocorrelation" Current Directions in Biomedical Engineering,vol. 2,No. 1, 2016, pp. 241-245. https://doi.org/10.1515/cdbme-2016-0054 (Year: 2016).*

Mafi, Mahsa. "Signal Processing Methods for Heart Rate Detection Using the Seismocardiogram." (2016). (Year: 2016).*

Zakrzewski, M. (2015). Methods for Doppler Radar Monitoring of Physiological Signals. (Tampere University of Technology. Publication; vol. 1315). Tampere: Tampere University of Technology. (Year: 2015).*

Viswanathan, Mathuranathan. Interpret FFT results—obtaining magnitude and phase information. GaussianWaves: Signal Processing for Communication Systems. Nov. 19, 2015. https://www.gaussianwaves.com/2015/11/interpreting-fft-results-obtaining-magnitude-and-phase-information/. (Year: 2015).*

Scalise, L. (Jan. 2012). "Non Contact Heart Monitoring," retrieved from https://www.researchgate.net/publicaton/221923114 Non Contact Heart Monitoring. (27 pages.).

* cited by examiner

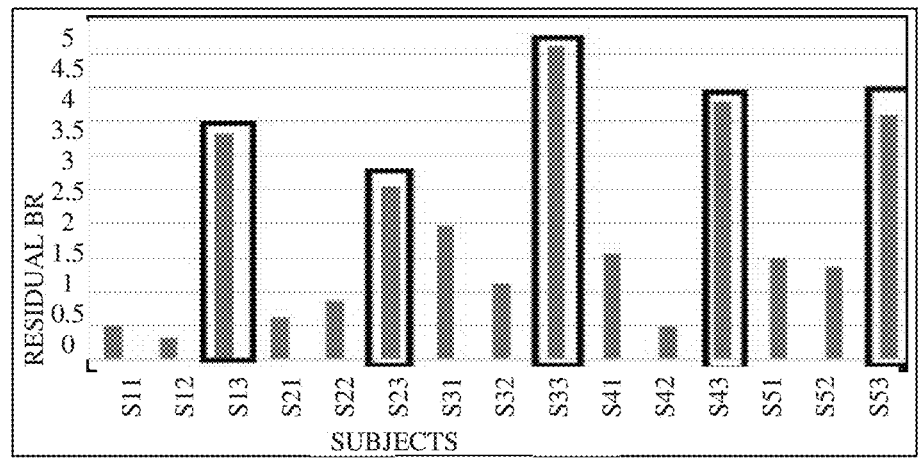
FIG. 8
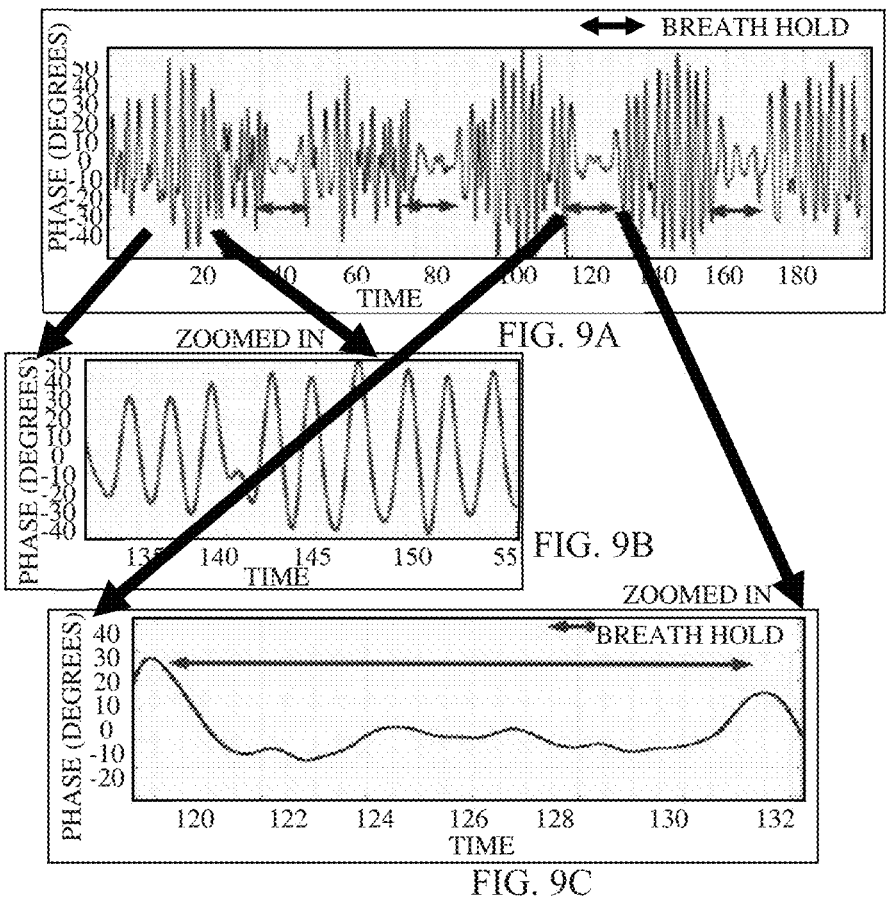
FIG. 9A
FIG. 9B
FIG. 9C

METHOD AND SYSTEM FOR NON-CONTACT BIO-SIGNAL DETECTION USING ULTRASOUND SIGNALS IN WHICH MAGNITUDE AND PHASE SIGNALS ARE OBTAINED FROM IN-PHASE AND QUADRATURE BASEBAND SIGNALS

PRIORITY CLAIM

This U.S. patent application claims priority under 35 U.S.C. § 119 to: India Application No. 201921030330, filed on Jul. 26, 2019. The entire contents of the aforementioned application are incorporated herein by reference.

TECHNICAL FIELD

The disclosure herein generally relates to bio-signal detection, and, more particularly, to method and system for non-contact bio-signal detection using ultrasound signal.

BACKGROUND

Usage of ultrasound signal is a widespread practice in medicine for various applications including bio-tissue imaging. Most recently, the technique is also exploited to detect physiological signals like heart sound or heart-beats through developed ultrasound stethoscopes. However, most of the sensing is based on contact-based measurements with the target, for example the human beings.

One of the main causes of using ultrasound in contact basis is due to the huge mismatch of acoustic impedance between air and human skin that results in reflecting most of the ultrasound energy back into air. This is also compounded by the fact that ultrasound gets absorbed fairly fast in air. Non-contact use of ultrasound for bio-signal detection from a distance is relatively limited. Typically, non-contact measurement utilizes Time of Flight (ToF) technique.

SUMMARY

Embodiments of the present disclosure present technological improvements as solutions to one or more of the above-mentioned technical problems recognized by the inventors in conventional systems. For example, in one embodiment, a method for non-contact bio-signal detection is provided. The method includes acquiring, via one or more hardware processors, an in-phase I(t) baseband signal and a quadrature Q(t) baseband signal associated with an ultrasound signal directed from the sensor assembly towards the target. Further, the method includes calculating, via the one or more hardware processors, magnitude and phase signals from the in-phase I(t) and quadrature Q(t) baseband signals. Also, the method includes filtering, via the one or more hardware processors, the magnitude and phase signals by passing through a band pass filter associated with a predefined frequency range to obtain filtered magnitude and phase signals. Moreover, the method includes identifying, by performing Fast Fourier Transformation (FFT) of the filtered magnitude and phase signals, frequency of dominant peaks of spectrum of the magnitude and phase signals in the ultrasound signal, via the one or more hardware processors. Additionally, the method includes determining, via the one or more hardware processors, value of a bio-signal associated with the target based on weighted values of the frequency of the dominant peaks of the magnitude and phase signals.

In another aspect, a system for non-contact bio-signal detection is provided. The system includes one or more memories; and one or more first hardware processors, the one or more first memories coupled to the one or more first hardware processors, wherein the one or more first hardware processors are configured to execute programmed instructions stored in the one or more first memories to acquire an in-phase I(t) baseband signal and a quadrature Q(t) baseband signal associated with an ultrasound signal directed from the sensor assembly towards the target. Further, the one or more hardware processors are configured by the instructions to calculate magnitude and phase signals from the in-phase I(t) and quadrature Q(t) baseband signals. Furthermore, the one or more hardware processors are configured by the instructions to filter the magnitude and phase signals by passing through a band pass filter associated with a predefined frequency range to obtain filtered magnitude and phase signals. Moreover, the one or more hardware processors are configured by the instructions to identify, by performing Fast Fourier Transformation (FFT) of the filtered magnitude and phase signals, frequency of dominant peaks of spectrum of the magnitude and phase signals in the ultrasound signal. Also, the one or more hardware processors are configured by the instructions to determine value of a bio-signal associated with the target based on weighted values of the frequency of the dominant peaks of the magnitude and phase signals.

In yet another aspect, a non-transitory computer readable medium for non-contact bio-signal detection. The method includes acquiring, via one or more hardware processors, an in-phase I(t) baseband signal and a quadrature Q(t) baseband signal associated with an ultrasound signal directed from the sensor assembly towards the target. Further, the method includes calculating, via the one or more hardware processors, magnitude and phase signals from the in-phase I(t) and quadrature Q(t) baseband signals. Also, the method includes filtering, via the one or more hardware processors, the magnitude and phase signals by passing through a band pass filter associated with a predefined frequency range to obtain filtered magnitude and phase signals. Moreover, the method includes identifying, by performing Fast Fourier Transformation (FFT) of the filtered magnitude and phase signals, frequency of dominant peaks of spectrum of the magnitude and phase signals in the ultrasound signal, via the one or more hardware processors. Additionally, the method includes determining, via the one or more hardware processors, value of a bio-signal associated with the target based on weighted values of the frequency of the dominant peaks of the magnitude and phase signals.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 8 illustrates plot showing a residual, i.e., the difference of BR-US and BR-manual, in accordance with an embodiment of the present disclosure.

FIG. 9A illustrates raw and BR-filtered unwrapped phase, in accordance with an embodiment of the present disclosure.

FIGS. 9B and 9C illustrate a small section of BR-filtered signal during normal breathing and breath-hold state, in accordance with an embodiment of the present disclosure.

DETAILED DESCRIPTION

Figure 1:
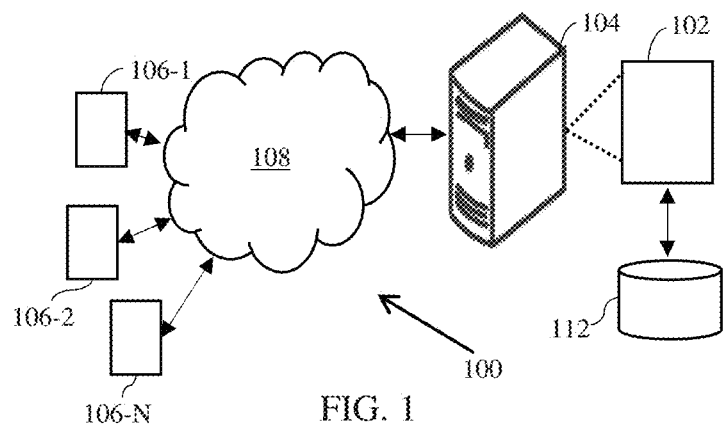
FIG. 1 illustrates a network environment implementing a system 102 for non-contact bio-signal detection using ultrasound signal, in accordance with an embodiment of the present disclosure.

Ultrasound has been widely used in medical field for centuries and predominately used for imaging and detection of physiological signals like heart sound or heart beats. However, most of the ultrasound sensing for monitoring bio-signals are all based on direct contact with human skin.

Usage of non-contact based methods for detection of bio-signals is limited. The non-contact detection of BR and HR may be useful in application, such as measuring the parameters for burn victims or for person infected with contagious viruses. Most of the non-contact BR/HR detection has been done with microwave radar using 10.6 GHz to 24 GHz frequency. However, since microwave can penetrate human tissue and can directly interact with the lung/heart walls, it may have some adverse effect on human tissues if power is not controlled properly. Moreover, working in GHz range may be challenging for both designing the antennas and the electronics. In addition, microwave may be not used on subjects/targets having pacemakers.

Ultrasound is safe for human exposure; moreover working in kHz range is much simpler. There are multiple contact based ultrasonic detection of HR and BR techniques available for various use-cases but non-contact detection of those are found to be limited. For example, a conventional method utilizes non-contact measurement of BR using ultrasound from smartphone exploits air attenuation, however, said technique is based on direct amplitude measurements. This usually provides low signal to noise ratio (S/N) as amplitude is easily corrupted by environmental noise and usually not recommended for measuring tiny signals.

Another conventional technique for measuring non-contact HR through clothes using ultrasound using pulse-Doppler principle, however the instrumentation required for such measurement is fairly complex as pulse-Doppler utilizes sharp pulses thus requiring sophisticated electronics.

Typically, non-contact based methods utilize ToF techniques for detection of bio-signals. Any ToF measurement requires generation of sharp pulses and timely detection of those which not only require sophisticated electronics design to cope with the speed of sound in air but also suffers from external noise as the receiver needs to be wideband to accept the sharp pulses.

Various embodiments described herein overcome these and other disadvantages of known techniques, and provide method and system that can facilitate in implementing simple yet sensitive measurements in detecting bio-signals through air-borne ultrasound. As is understood, herein the respiration and heart pumping contributes to the movement of chest wall of the subject. When an ultrasound signal is impinged towards the subject, the transmitted ultrasound signal and the reflected ultrasound signal are utilized for non-contact bio-signal detection. In an example embodiment, the method for non-contact bio-signal detection includes measuring in-phase and quadrature signals obtained based on a difference in phase between the transmitted and received ultrasonic signals. In particular, the reflected signal from the target's/subject's body is analyzed. Herein, movement of chest wall of the target/subject interacts with the impinging ultrasound beam targeted towards the target (such as a human being) and modulates reflected beam accordingly. In an embodiment, the disclosed system utilizes measurements from the magnitude and phase signals associated with the ultrasound signal (transmitted and reflected signals to detect the bio-signal. It will be noted that in the following description, the terms "amplitude" and "magnitude" will be interchangeably used.

The disclosed system extracts vital information from the reflected wave if sensitive measurement is taken. In an embodiment, a Vector Network Analyzer (VNA) is disclosed that facilitates in taking measurements for detection of bio-signals. The disclosed method, system and the VNA are described further in the description below.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Referring now to the drawings, and more particularly to FIG. 1 through 12, where similar reference characters denote corresponding features consistently throughout the figures, there are shown preferred embodiments and these embodiments are described in the context of the following exemplary system and/or method.

FIG. 1 illustrates a network environment 100 implementing a system 102 for non-contact bio-signal detection using ultrasound signal, according to an embodiment of the present subject matter. Herein, the bio-signal may include 'heart rate' signal or/and a 'breathing rate' signal of a target (or a subject). In an embodiment, the disclosed system 102 is capable of detecting the heart rate and/or breathing rate of a subject in a non-contact manner. As is understood, herein the 'non-contact' manner may refer to detection of the bio-signals without establishing physical contact between the subject and a device embodying the system 102.

In an implementation, an ultrasound signal is directed towards the target, and the system 102 is configured to acquire in-phase I(t) baseband signal and a quadrature Q(t) baseband signal associated with the ultrasound signal. In an embodiment, the ultrasound signal may be directed by using a sensor assembly. An example of the sensor assembly is described further with reference to FIG. 4.

In an embodiment, the system 102 may be embodied in the sensor assembly. Alternatively, the system 102 may be embodied in a computing device, for instance a computing device 104 communicably coupled with the sensor assembly. In an embodiment, the computing device may be an example of a server. Herein, although the present disclosure is explained considering that the system 102 is implemented on a server, it may be understood that the system 102 may also be implemented in a variety of computing systems, such as a laptop computer, a desktop computer, a notebook, a workstation, a cloud-based computing environment and the like. In one implementation, the system 102 may be implemented in a cloud-based environment. It will be understood that the system 102 may be accessed by multiple devices such as devices 106-1, 106-2 . . . 106-N, collectively referred to as devices 106 hereinafter, or applications residing on the user devices 106. Examples of the devices 106 may include, but are not limited to, a portable computer, a personal digital assistant, a handheld device, a Smartphone, a Tablet Computer, a workstation and the like. The devices 106 are communicatively coupled to the system 102 through a network 108.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 108 may include a variety of network devices, including routers, bridges, servers, computing devices, storage devices. The network devices within the network 108 may interact with the system 102 through communication links.

As discussed above, the system 102 may be implemented in the computing device 104, such as a hand-held device, a laptop or other portable computer, a tablet computer, a mobile phone, a PDA, a smartphone, and a wearable device such as a smart watch. The system 102 may also be implemented in a workstation, a mainframe computer, a server, and a network server. In an embodiment, the system 102 may be coupled to a data repository, for example, a repository 112. The repository 112 may store data processed, received, and generated by the system 102. In an alternate embodiment, the system 102 may include the data repository 112. The components and functionalities of the system 102 for non-contact bio-signal detection are described further in detail with reference to FIGS. 2-6.

Figure 2:
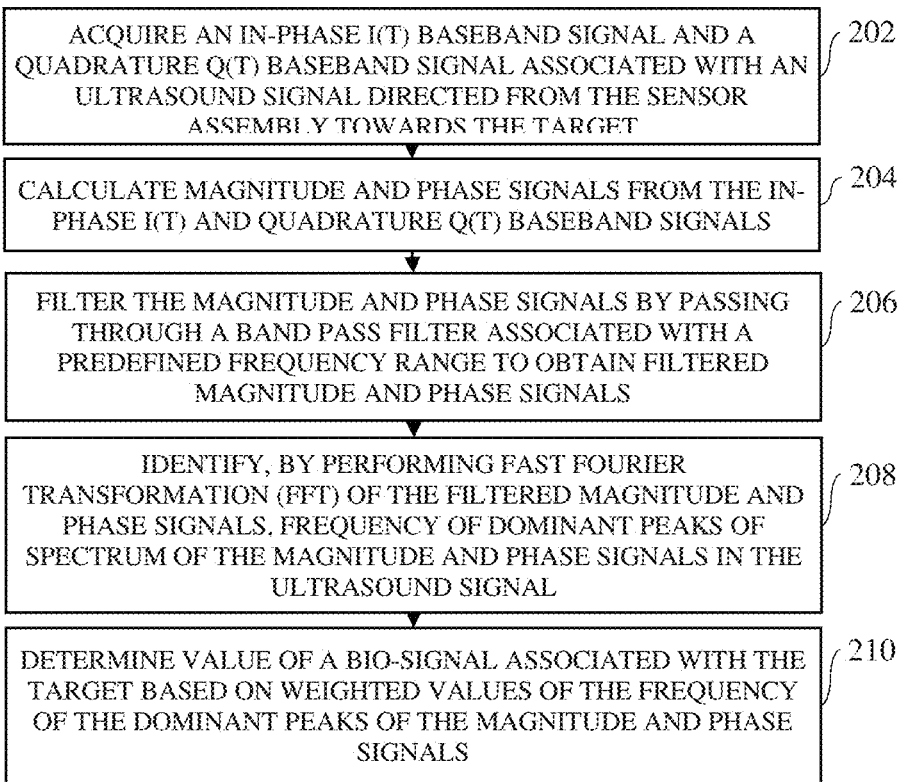
FIG. 2 is a flow diagram for a method for non-contact bio-signal detection using ultrasound signal, in accordance with an embodiment of the present disclosure.
Figure 3:
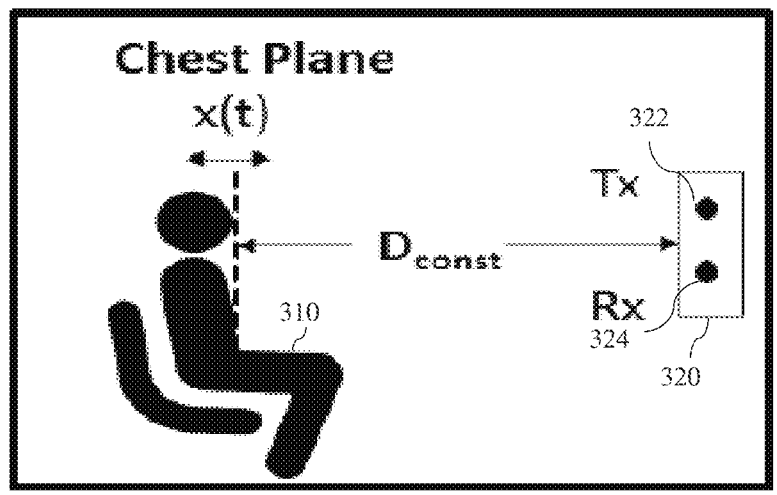
FIG. 3 illustrates an example set-up utilized for implementation of the disclosed non-contact bio-signal detection system, in accordance with an embodiment of the present disclosure.
Figure 4:
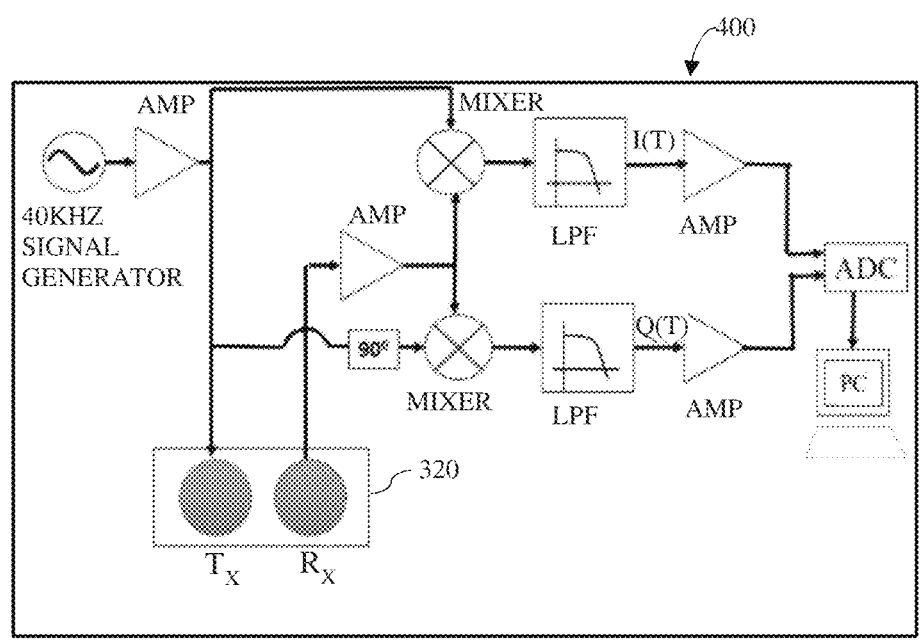
FIG. 4 illustrates example VNA architecture for non-contact bio-signal detection, in accordance with an embodiment of the present disclosure.
Figure 5:
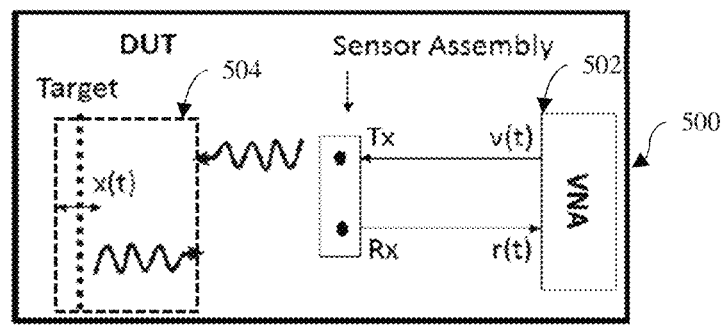
FIG. 5 illustrates application of the VNA of FIG. 4 for non-contact bio-signal detection, in accordance with an embodiment of the present disclosure.
Figure 6:
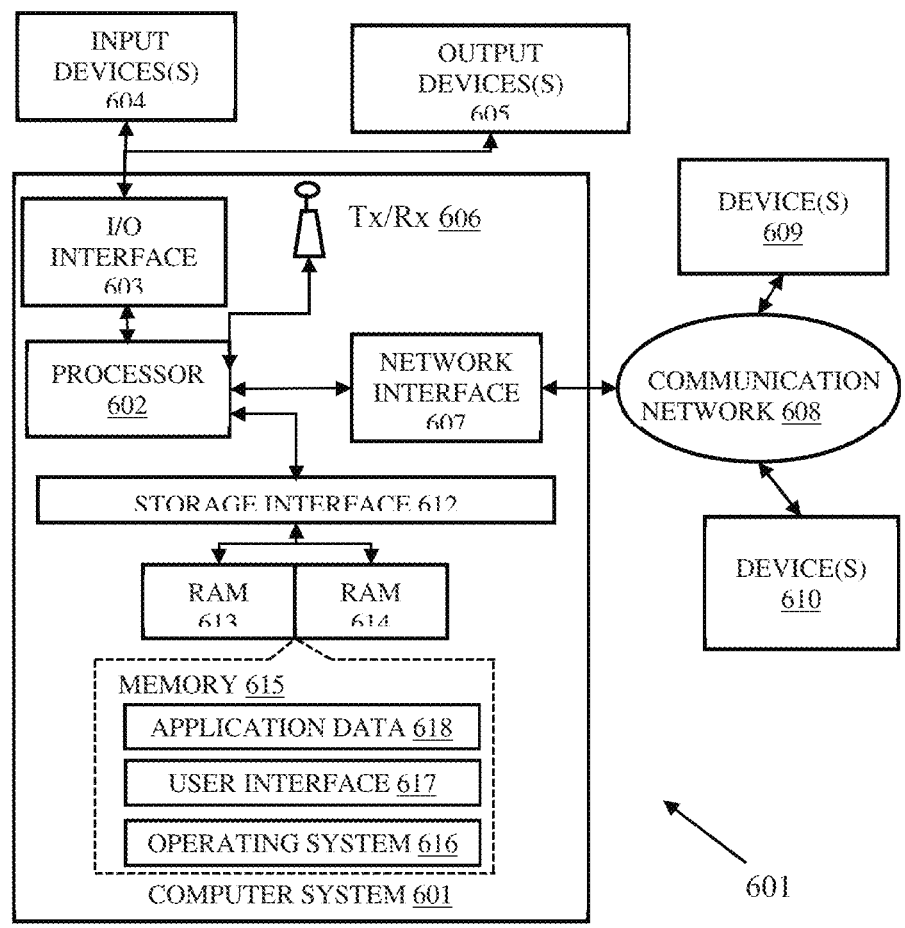
FIG. 6 illustrates block diagram of an exemplary computer system for implementing embodiments consistent with the present disclosure.

FIGS. 2-6 describe method, an example set-up, and system implementation for non-contact bio-signal detection, in accordance various embodiments of present disclosure. For example, FIG. 2 illustrates a flow-diagram of a method for non-contact bio-signal detection in accordance with an example embodiment. FIG. 3 illustrates an example set-up utilized for implementation of the disclosed non-contact bio-signal detection system, in accordance with an example embodiment of the present disclosure. FIG. 4 illustrates example VNA architecture for non-contact bio-signal detection, in accordance with an example embodiment of the present disclosure. FIG. 5 illustrates application of the VNA of FIG. 4 for non-contact bio-signal detection, in accordance with an example embodiment of the present disclosure. FIG. 6 illustrates block diagram of an exemplary computer system for implementing embodiments consistent with the present disclosure. FIGS. 2-6 may hereinafter be collectively referred for description of non-contact bio-signal detection.

At 202 (FIG. 2), the method 200 includes acquiring an in-phase I(t) baseband signal and a quadrature Q(t) baseband signal associated with an ultrasound signal. In an embodiment, the in-phase I(t) and quadrature Q(t) baseband signals are acquired by using a sensor assembly, for example a sensor assembly described with reference to FIGS. 3-5.

Referring to FIG. 3, for the bio-signal detection for a target (for example a target 310, FIG. 3), the target 310 may be made to sit in front of a sensor assembly, for example the sensor assembly 320. The sensor assembly 320 may be placed in line-of-sight of target (subject's chest) for detection of the bio-signal, and ultra sound signal is directed from the sensor assembly towards the target.

In an embodiment, the sensor assembly 320 may include a first transducer (for example, a transducer 322) for excitation of the target 310 with the ultrasound signal and a second transducer (for example, a transducer 324) for receiving a reflected signal Rx from the target 310. In an embodiment, the first and the second transducers may include ultrasound air-couple transducers. The first transducer 322 is used for excitation with ultrasound frequency 40 KHz (i.e. transmitter Tx) and the second transducer 324 is used to receive the reflected signal (i.e. a receiver Rx). As is seen here, the transmitter and the receiver are placed in one plane and the target is placed opposite to them. An example of a circuit 400 implemented for detection of non-contact bio-signal using ultrasound signals is illustrated with reference to FIG. 4, where the in-phase I(t) and quadrature Q(t) baseband signals are acquired from the sensor assembly 320.

At 204, the method 200 includes calculating magnitude and phase signals from the in-phase I(t) and quadrature Q(t) baseband signals. The phase shift is related to wave travel path by equation (1):

$$\emptyset = \frac{2\pi t}{T} = \frac{2\pi}{T} X \frac{L}{c} \quad (1)$$

where, Ø is the phase shift, T is the time period of oscillating wave, L is the travel path, and c is the velocity of sound in air.

It is assumed that the sensor assembly (Tx, Rx) is at a distance $D_{const}$ from the mean position of the chest wall of the target. The chest wall motion x(t) has both breathing amplitudes (or magnitude) and heart amplitudes (or magnitude) imparted on it as a linear superposition and can be mathematically represented as:

$$x(t) = a_b \sin(2\pi f_b t) + a_h \sin(2\pi f_h t)$$

where, $a_b$ and $a_h$ is amplitude (or magnitude) of chest wall movement due to breathing and heart respectively, $f_b$ is breathing frequency, and $f_h$ is heart frequency.

The phase difference between the Tx and Rx can be found using equation (1) as:

$$\varnothing(t) = 4\pi/Tc[Dconst + x(t)] \quad (2)$$

i.e, $\varnothing(t) = 4\pi/TcDconst + 4\pi/Tcx(t)$ (3)

i.e, $\varnothing = \varnothing D + \varnothing x$ (4)

where, ØD contributes to a constant DC term and Øx will capture the periodic motion of the breathing and heart.

Applying a proper filter (around fb and fh) facilitates in extracting the bio-signals (for example, heart or breathing signals) as fb and fh usually occupy different frequency bands. At 206, method 200 includes filtering the magnitude and phase signals by passing through a band pass filter associated with a predefined frequency range to obtain filtered magnitude and phase signals. In an embodiment, the predefined frequency range to obtain filtered magnitude signal is (0.2-0.9 Hz) and for the phase signals is (0.9-3 Hz). Hence, $BPF_{BR} = (0.2 - 0.9 \text{ Hz})$, and $BPF_{HR} = (0.9 - 3 \text{ Hz})$ Once the magnitude and phase signals are extracted/filtered, Fast Fourier Transformation (FFT) can be used to measure the HR and BR. At 208, Fast Fourier Transformation (FFT) of the filtered magnitude and phase signals is preformed to identifying frequency of dominant peaks of spectrum of the magnitude and phase signals in the ultrasound signal. For example, $\text{Freq}[BPF_{BR}(\text{Mag})] = Fr_{BR}^{Mag}$.

In an embodiment, the VNA interacts with a Device under Test (DUT), for example, an air column along the moving chest wall of the target. An example DUT 502 interacting with a VNA 504 is illustrated in FIG. 5. In an embodiment, the VNA 504 is capable of measuring phase and gain information of both reflected and transmitted signal while an excitation passes the DUT 502. Usually, a DUT is excited with a reference sinusoid from the VNA and the response (i.e. amplitude and phase) is observed for the transmitted and reflected signals from the DUT. Herein, v(t) is the excitation to a DUT from the VNA and r(t) is the corresponding response as shown in FIG. 5
where $$v(t) = A \cos(2\pi ft) \quad (5)$$

$$v(t) = A' \cos(2\pi ft + \varnothing) \quad (6)$$

The VNA gives accurate measurement of gain and phase information as, Gain=r(t)/v(t) and Phase=Ø.

The r(t) and Ø is measured through phase sensitive measurement principle to achieve very high S/N for measuring tiny signals. The response of DUT is multiplied ($M_I$) and Filtered ($Filter_I$) by the excitation reference in one channel and the same is done ($MQ$ followed by $Filter_Q$) in another channel except the multiplication is performed with a quadrature signal with respect to the excitation signal. Mathematically, the output at MI and the low pass filter, $Filter_I$ is given in equation (7) and (8) respectively, as follows:

$$A \cos(2\pi ft) \times A' \cos(2\pi ft + \varnothing) \quad (7)$$

i.e., $A'/2.[\cos(4\pi ft) + \cos(\varnothing)]$ AA'/2 $\cos(\varnothing)$ (8)

So the I channel is proportional to the signal amplitude (or magnitude) (r(t)), as depicted in eqn. (9).

$$I \propto A'/2 \cos(\varnothing) \quad (9)$$

The quadrature component Q is generated just like the In-phase signal, except the fact that it is 90 degrees out of phase with respect to v(t). Hence, Q is given by eqn. (11).

$$Q \propto A'/2 \sin(\varnothing) \quad (11)$$

It can be seen that both I and Q are at DC enabling implementation of narrowband filtering which in turn increases the S/N for the measurements. I and Q are then combined and scaled to get amplitude (or magnitude) and phase (Ø) information of r(t) according to eqn. (12) and (13).

$$\text{Amplitude(or magnitude)} = \sqrt{(I^2 + Q^2)} \quad (12)$$

$$\varnothing = \tan^{-1}(Q/I) \quad (13)$$

Herein the DUT is the air column along with moving object (chest wall) as depicted in FIG. 5. The excitation enters the DUT through Tx, gets reflected by the moving targets and ends in Rx. The constant air column between the Tx/Rx and target ($D_{const}$ in section) does not play much role and it is only the 'd' or x(t) that changes the response (phase response) of the DUT that carries the intended information. In an embodiment, an unwrapped phase may be used for all calculations. In an embodiment, an unwrapped phase is utilized as the wrapped phase is prone to noise due to which useful information may be lost. In practical scenarios, the phase change is not constrained in ±π, however the phase varies much beyond that value. Hence, the wrapping of the phase occurs, thereby leading to random phase wrapping. To get rid of the problems associated with random phase wrapping, in the present embodiment, unwrapped phase is utilized.

Referring back to FIG. 2, at 210, the method 200 includes determining value of a bio-signal associated with the target based on weighted values of the frequency of the dominant peaks of the magnitude and phase signals. In an embodiment, when the bio-signal is breath rate of the target, the value of the bio-signal is determined based on the equation:

$$BR = \text{int}[\alpha_1 . BR_{Mag} + (1 - \alpha_1) . BR_{ph}] \quad (14)$$

where, $BR_{Mag}$ is the frequency of the most dominant peak in breaths per minute and is obtained by multiplying the frequency of the most dominant peak of the magnitude signal with 60, $BR_{Ph}$ is the frequency of the most dominant peak in breaths per minute and is obtained by multiplying the frequency of the most dominant peak of the phase signal with 60, and $\alpha_1$ is a real number having value between (and including) 0 and 1.

In another embodiment, when the bio-signal is heart rate of the target, the value of the bio-signal is determined based on the equation:

$$HR = \text{int}[\alpha_2 . HR_{Mag} + (1 - \alpha_2) . HR_{ph}] \quad (15)$$

$HR_{Mag}$ is the frequency of the most dominant peak in heart-beats per minute and is obtained by multiplying the frequency of the most dominant peak of the magnitude signal with 60, and $HR_{Ph}$ is the frequency of the most dominant peak in heart-beats per minute and is obtained by multiplying the frequency of the most dominant peak of the phase signal with 60.

As seen here, the heart rate and the breathing rate are determined based on the equations (14) and (15). The aforementioned non-contact method of detecting HR and BR combines both amplitude and phase from the in-phase and quadrature signatures of the phase difference between the transmitted and received ultrasound signals in a unique way (as presented in equations (14) and (15)). It will be noted herein that the aforementioned manner of combining the amplitude and phase from the in-phase and quadrature signatures of the phase difference between transmitted and received signals for non-contact detection of HR and BR has the technical advantage of providing accurate results when compared to the conventional techniques and systems. For instance, the mean residual error of HR and BR computed using the disclosed embodiments are determined to be 4.5 beats per minute and 1.87 breaths per minute, respectively. An example scenario of computing the HR and BR using the disclosed embodiments, and results thereof are discussed further with reference with FIGS. 7A-12. An example of a computer system for a system for non-contact bio-signal detection is described further with reference to FIG. 6.

FIG. 6 is a block diagram of an exemplary computer system 601 for implementing embodiments consistent with the present disclosure. The computer system 601 may be implemented in alone or in combination of components of the system 102 (FIG. 1). Variations of computer system 601 may be used for implementing the devices included in this disclosure. Computer system 601 may comprise a central processing unit ("CPU" or "hardware processor") 602. The hardware processor 602 may comprise at least one data processor for executing program components for executing user- or system-generated requests. The processor may include specialized processing units such as integrated system (bus) controllers, memory management control units, floating point units, graphics processing units, digital signal processing units, etc. The processor may include a microprocessor, such as AMD Athlon™, Duron™ or Opteron™, ARM's application, embedded or secure processors, IBM PowerPC™, Intel's Core, Itanium™, Xeon™, Celeron™ or other line of processors, etc. The processor 602 may be implemented using mainframe, distributed processor, multi-core, parallel, grid, or other architectures. Some embodiments may utilize embedded technologies like application specific integrated circuits (ASICs), digital signal processors (DSPs), Field Programmable Gate Arrays (FPGAs), etc.

Processor 602 may be disposed in communication with one or more input/output (I/O) devices via I/O interface 603. The I/O interface 603 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.11 a/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using the I/O interface 603, the computer system 601 may communicate with one or more I/O devices. For example, the input device 604 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc.

Output device 605 may be a printer, fax machine, video display (e.g., cathode ray tube (CRT), liquid crystal display (LCD), light-emitting diode (LED), plasma, or the like), audio speaker, etc. In some embodiments, a transceiver 606 may be disposed in connection with the processor 602. The transceiver may facilitate various types of wireless transmission or reception. For example, the transceiver may include an antenna operatively connected to a transceiver chip (e.g., Texas Instruments WiLink WL1283, Broadcom BCM4750IUB8, Infineon Technologies X-Gold 618-PMB9800, or the like), providing IEEE 802.11a/b/g/n, Bluetooth, FM, global positioning system (GPS), 2G/3G HSDPA/HSUPA communications, etc.

In some embodiments, the processor 602 may be disposed in communication with a communication network 608 via a network interface 607. The network interface 607 may communicate with the communication network 608. The network interface may employ connection protocols including, without limitation, direct connect, Ethernet (e.g., twisted pair 10/100/1000 Base T), transmission control protocol/internet protocol (TCP/IP), token ring, IEEE 802.11a/b/g/n/x, etc. The communication network 608 may include, without limitation, a direct interconnection, local area network (LAN), wide area network (WAN), wireless network (e.g., using Wireless Application Protocol), the Internet, etc. Using the network interface 607 and the communication network 608, the computer system 601 may communicate with devices 609 and 610. These devices may include, without limitation, personal computer(s), server(s), fax machines, printers, scanners, various mobile devices such as cellular telephones, smartphones (e.g., Apple iPhone, Blackberry, Android-based phones, etc.), tablet computers, eBook readers (Amazon Kindle, Nook, etc.), laptop computers, notebooks, gaming consoles (Microsoft Xbox, Nintendo DS, Sony PlayStation, etc.), or the like. In some embodiments, the computer system 601 may itself embody one or more of these devices.

In some embodiments, the processor 602 may be disposed in communication with one or more memory devices 615 (e.g., RAM 613, ROM 614, etc.) via a storage interface 612. The storage interface may connect to memory devices including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc. Variations of memory devices may be used for implementing, for example, any databases utilized in this disclosure.

The memory devices 615 may store a collection of program or database components, including, without limitation, an operating system 616, user interface application 617, user/application data 618 (e.g., any data variables or data records discussed in this disclosure), etc. The operating system 616 may facilitate resource management and operation of the computer system 601. Examples of operating systems include, without limitation, Apple Macintosh OS X, Unix, Unix-like system distributions (e.g., Berkeley Software Distribution (BSD), FreeBSD, NetBSD, OpenBSD, etc.), Linux distributions (e.g., Red Hat, Ubuntu, Kubuntu, etc.), IBM OS/2, Microsoft Windows (XP, Vista/7/8, etc.), Apple iOS, Google Android, Blackberry OS, or the like. User interface 617 may facilitate display, execution, interaction, manipulation, or operation of program components through textual or graphical facilities. For example, user interfaces may provide computer interaction interface elements on a display system operatively connected to the computer system 601, such as cursors, icons, check boxes, menus, scrollers, windows, widgets, etc. Graphical user interfaces (GUIs) may be employed, including, without limitation, Apple Macintosh operating systems' Aqua, IBM OS/2, Microsoft Windows (e.g., Aero, Metro, etc.), Unix X-Windows, web interface libraries (e.g., ActiveX, Java, Javascript, AJAX, HTML, Adobe Flash, etc.), or the like.

In some embodiments, computer system 601 may store user/application data 618, such as the data, variables, records, etc. as described in this disclosure. Such databases may be implemented as fault-tolerant, relational, scalable, secure databases such as Oracle or Sybase. Alternatively, such databases may be implemented using standardized data structures, such as an array, hash, linked list, structured text file (e.g., XML), table, or as hand-oriented databases (e.g., using HandStore, Poet, Zope, etc.). Such databases may be consolidated or distributed, sometimes among various computer systems discussed above. It is to be understood that the structure and operation of any computer or database component may be combined, consolidated, or distributed in any working combination.

Additionally, in some embodiments, the server, messaging and instructions transmitted or received may emanate from hardware, including operating system, and program code (i.e., application code) residing in a cloud implementation. Further, it should be noted that one or more of the systems and methods provided herein may be suitable for cloud-based implementation. For example, in some embodiments, some or all of the data used in the disclosed methods may be sourced from or stored on any cloud computing platform.

Example Scenario:

In an example scenario, the breath rate (BR) and the heart rate (HR) are computed through the above-mentioned method 200, over 50 trials, each one-minute long. The calculated HR, BR are compared with HR obtained from PPG sensor, and manually counted BR respectively. It is found that $\alpha_1 = \alpha_2 = 0.2$ yields best accuracy. An example experimentation for detecting bio-signals for instance HR and BR is described below further with reference to FIGS. 7A-12.

In an example scenario, 40 kHz air-couple transducers and a Vector Network Analyzer or VNA (Bode100 from Omicorn Labs™ were used for the measurements pertaining to detection of bio-signals. Matlab™ scripts were used to control the VNA and process the acquired data (off-line). A typical voltage of 5.72V was applied to excite the air-couple transducer for all the measurements. Five subjects (age 32±6 years, 3 male and 2 female) took part in the experiments.

For this a SPO2 device, providing instantaneous HR values (in beats/min), was used to record the HR data. For BR ground truth, one human observer was employed to observe the abdomen and chest wall movements of the subject and counted the breathing cycles. 3 trials of data from each of 5 subjects were recorded, all of which were 196 sec long. For each of the subject, during the last trial of data-collection, the experimenter gave periodic verbal instructions 4 times to hold the breath for 10 seconds or till the point he/she could, whichever came earlier. Herein, it will be noted that breathing is a slow and periodic signal and is generally quite easily observable by naked eye and hence a human observer was appointed to get most accurate counts. In this BR/HR experiment, the sensor assembly was put in line-of sight with the left portion of the chest of the target/subject and the subject was instructed to be seated, relaxing on a back rested chair, to minimize any body movement (for example, as illustrated in FIG. 3). In addition, in a separate experiment, the accuracy of the SPO2 device was checked. Here it took one min of SPO2 readings for three trials, for each of three subjects while counting their pulses (i.e. heart beats in one minute by touching their wrist with a finger by a trained person).

The results obtained during this study are presented in this section. The data are acquired and analyzed offline in MATLAB™ 2018a. The VNA provides gain-magnitude and phase (wrapped and unwrapped) signals during two-port gain measurement. The acquired wrapped and unwrapped phase signal are filtered using a 4th order Butterworth band pass filter of bandwidth 0.1-0.8 Hz, in order to extract the BR filtered signal, i.e., the signal filtered to obtain the breath rate (BR). The bandwidth is so selected keeping in mind the breathing rate (per minute) range.

Figure 7A:
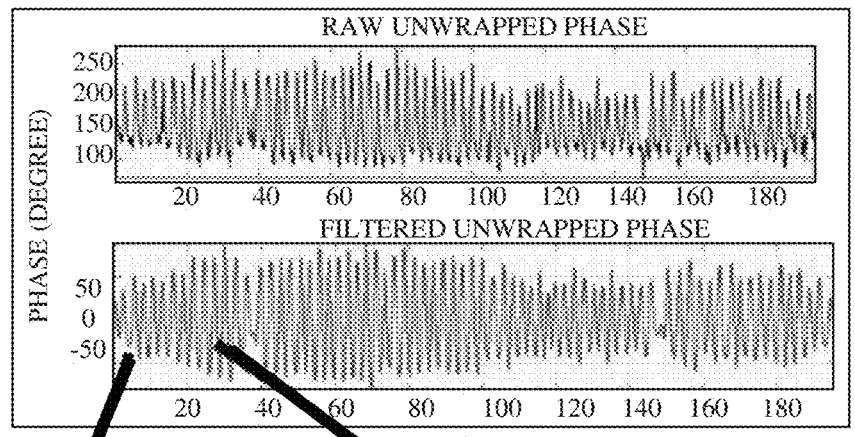
FIGS. 7A-7C illustrates raw and filtered unwrapped phase signals for non-contact bio-signal detection, in accordance with an embodiment of the present disclosure.
Figure 7B:
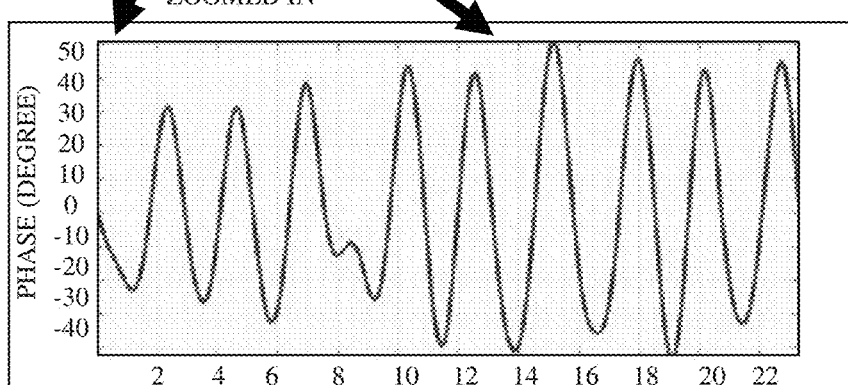
Figure 7C:
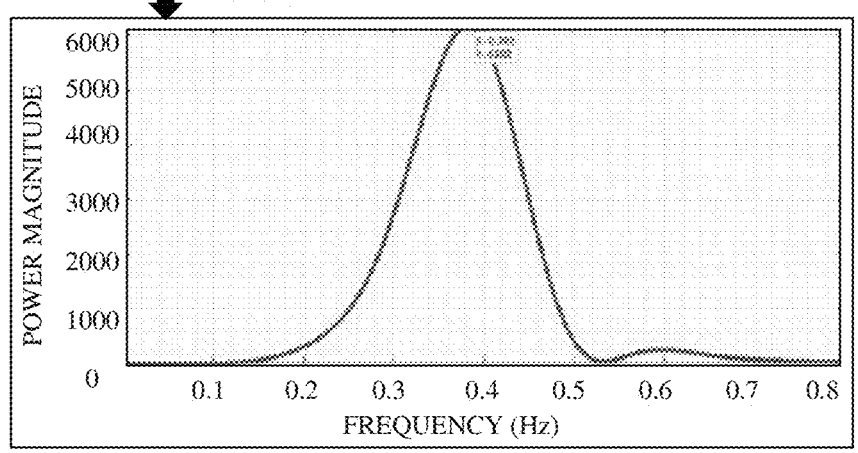

FIGS. 7A-7C illustrates the raw and filtered unwrapped phase signals. As illustrated, the multiple phase wraps in the wrapped phase signal, introduces additional, anonymous noise in the breath signals. Thus, the experiment was proceeded with the unwrapped phase signal for analyzing BR and HR filtered signal. FIG. 7B, represent a zoomed in BR filtered signal and its corresponding power spectral density is given in FIG. 7C. Power spectral density (PSD) is computed using Welch approach with a hamming window of length ten times the sampling rate and no overlapping. For the particular trail, whose PSD is shown in FIG. 7C, the dominant peak is at 0.358 Hz. Thus, the computed BR is 21.48 breaths per minute.

During the BR-HR experiments, 3 trials of five subjects were recorded, each trial lasting for duration of a bit more than 3 minutes (196 seconds to be precise). Thus there were a total 15 subject-trial instances ($S_{ij}$, where i=subject no, j=trial no).

Table I below presents the BR calculated from the ultrasound (BRUS) and manual breath count (BR-Manual) by the observer.

TABLE I

| $S_{ij}$ | BR-Manual | BR-US |
|---|---|---|
| S11 | 22 | 22.5 |
| S12 | 20 | 19.68 |
| S13 | 24 | 20.4 |
| S21 | 19 | 19.63 |
| S22 | 20 | 19.14 |
| S23 | 22 | 19.46 |
| S31 | 19 | 22.93 |
| S32 | 21 | 25.62 |
| S33 | 16 | 14.88 |
| S41 | 19 | 21.56 |
| S42 | 19 | 22.8 |
| S43 | 18 | 17.52 |
| S51 | 15 | 16.5 |
| S52 | 20 | 21.36 |
| S53 | 22 | 22.9 |

The residual, i.e., the difference of BR-US and BR manual is illustrated in FIG. 8.

FIG. 9A shows raw and BR-filtered unwrapped phase, where there are durations of breath hold that can be clearly observed. A small section of BR-filtered signal during normal breathing and breath-hold state is shown in FIG. 9B and FIG. 9C.

Figure 10B:
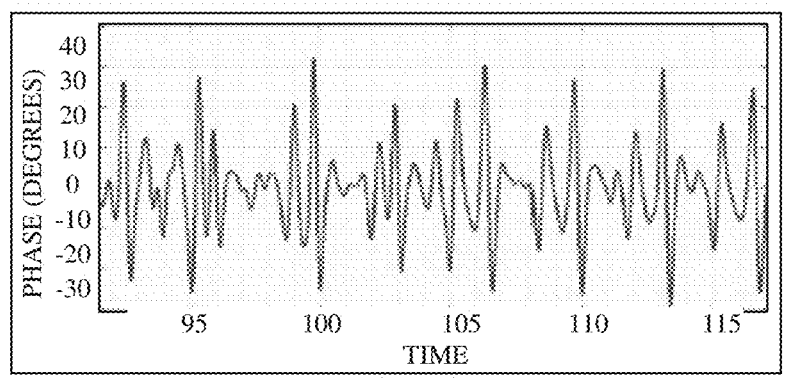
FIG. 10B illustrates a PSD corresponding to the HR-filtered signal of FIG. 10A, in accordance with an embodiment of the present disclosure.
Figure 10A:
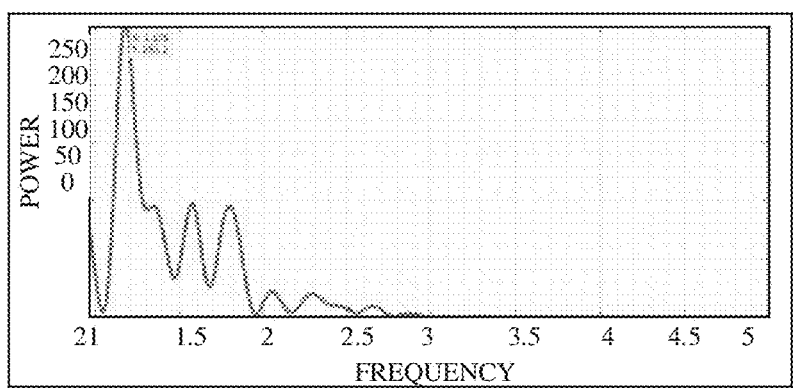
FIG. 10A illustrates a zoomed in HR-filtered signal, during normal breathing state, in accordance with an embodiment of the present disclosure.

For Heart Rate detection, the unwrapped phase signal, obtained during the BR-HR experiment is filtered using a 4th order butterworth bandpass filter with a bandwidth of 0.9-3 Hz, in order to obtain the HR filtered signal. A zoomed in HR-filtered signal, during normal breathing state is shown in FIG. 10A, and its corresponding PSD is shown in FIG. 10B.

Figure 11A:
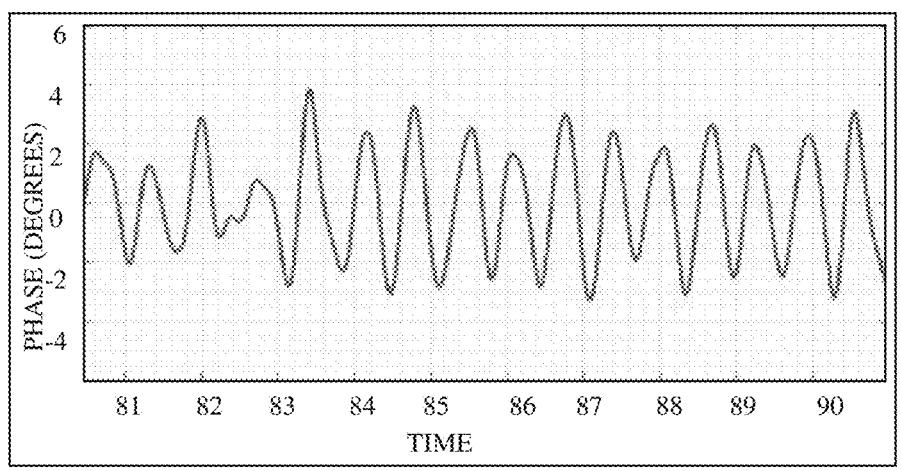
FIG. 11A shows a small window of HR-filtered signal while the subject held his/her breath for non-contact bio-signal detection, in accordance with an embodiment of the present disclosure.
Figure 11B:
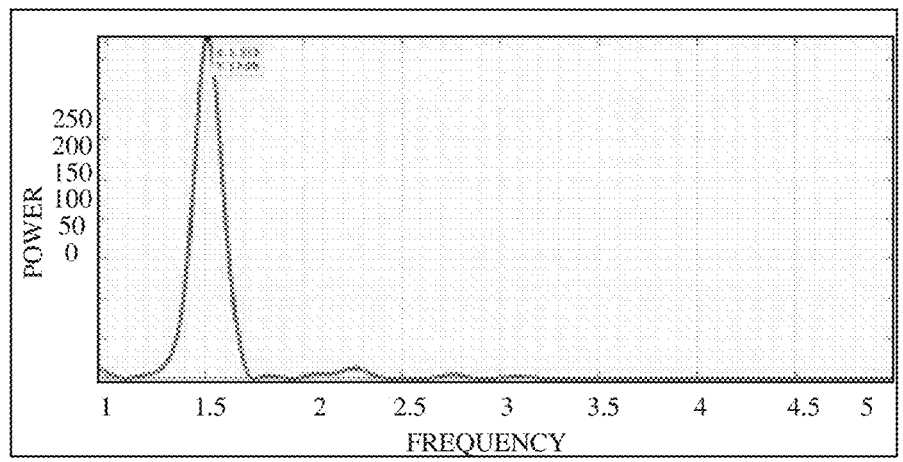
FIG. 11B illustrates a PSD corresponding to the HR-filtered signal of FIG. 11A, in accordance with an embodiment of the present disclosure.

FIG. 11A shows a small window of HR-filtered signal while the subject held his/her breath. Since during this particular window the breathing was held (pertaining to almost no breathing), the HR-filtered signal is much cleaner with distinct peaks and troughs. From the PSD of this signal (FIG. 11B) only one dominant peak is observed compared to multiple prominent peaks in the PSD of HR filtered signal. For calculating the heart rate, the frequency at which the dominant peak occurred is identified, and then is multiplied with 60 to get the heart rate in beats per minute. It was observed previously that there remains a difference of 2-3 beats per minute between the SPO2 recorded HR and the manual counts. Table II below presents the HR calculated from the SPO2 (HR-SPO2) and HR calculated from the unwrapped phase of the ultrasound (HR-US), computer over the complete duration of 196 seconds.

TABLE II

| Sij | HR-SPO2 | HR-US |
|---|---|---|
| S11 | 69 | 68.76 |
| S12 | 71 | 69.66 |
| S13 | 72 | 62.1 |
| S21 | 92 | 91.86 |
| S22 | 89 | 84.98 |
| S23 | 89 | 78.18 |
| S31 | 67 | 66.72 |
| S32 | 67 | 66.12 |
| S33 | 72 | 77.88 |
| S41 | 74 | 72.3 |
| S42 | 70 | 65.1 |
| S43 | 79 | 90.42 |
| S51 | 88 | 87.24 |
| S52 | 87 | 86.48 |
| S53 | 87 | 72.3 |

Figure 12:
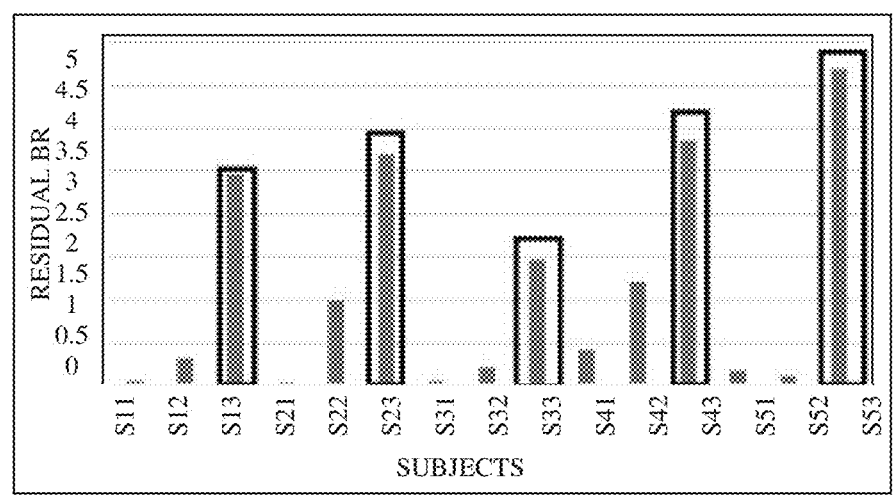
FIG. 12 illustrates plot showing a residual, i.e., the difference of HR-US and HR-manual, in accordance with an embodiment of the present disclosure.

The residual HR of the same are shown in FIG. 12. It is observed that the mean residual HR is 4.50 beats per minute over all the 15 subject-instances. For certain instances, (S13, S23, S33, S43, S53) where there were periods of breath hold, the residual HR is more compared to other instances.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

Various embodiments disclosed herein provides method and system for non-contact bio-signal detection using ultrasound signals. In an embodiment, embodiment, the disclosed method of detecting HR and BR combines both amplitude and phase from the in-phase and quadrature signatures of the phase difference between the transmitted and received ultrasound signals in a unique way. The aforementioned manner of combining the amplitude and phase from the in-phase and quadrature signatures of the phase difference between transmitted and received signals for non-contact detection of HR and BR has the technical advantage of providing accurate results when compared to the conventional techniques and systems. For instance, the mean residual error of HR and BR computed using the disclosed embodiments are determined to be 4.5 beats per minute and 1.87 breaths per minute, respectively.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor implemented method for non-contact bio-signal determination, comprising:
acquiring, via one or more hardware processors, an in-phase I(t) baseband signal and a quadrature Q(t) baseband signal associated with an ultrasound signal directed from a sensor assembly towards a target;

calculating, via the one or more hardware processors, magnitude, and phase signals from the in-phase I(t) and quadrature Q(t) baseband signals, wherein the magnitude and phase signals are obtained from the In-phase I(t) and the quadrature Q(t) baseband signals using the equations:

Magnitude, Mag=$\sqrt{I^2(t)+Q^2(t)}$

Phase, $\emptyset$=tan−1 (Q/I), wherein I channel is proportional to magnitude r(t) as I∝A'/2 cos ($\emptyset$), and quadrature channel is 90 degrees out of phase with respect to an excitation signal v(t) as Q∝A'/2 sin ($\emptyset$), wherein the phase $\emptyset$ is unwrapped as a chest wall movement x(t) of the target changes the phase response carrying intended information, wherein x(t)=$\alpha_b$ sin (2πf b t)+$\alpha_h$ sin (2πf h t) where, $\alpha_b$ and $\alpha_h$ is magnitude of the chest wall movement based on breathing and heart respectively, $f_b$ is breathing frequency, and $f_h$ is heart frequency;

filtering, via the one or more hardware processors, the magnitude and phase signals by passing through a band pass filter associated with a predefined frequency range to obtain filtered magnitude and phase signals;

identifying, via the one or more hardware processors by performing Fast Fourier Transformation (FFT) of the filtered magnitude and phase signals, frequency of dominant peaks of spectrum of the magnitude and phase signals in the ultrasound signal; and determining, via the one or more hardware processors, value of a bio-signal associated with the target based on weighted values of the frequency of the dominant peaks of the magnitude and phase signals.

2. The processor implemented method of claim 1, wherein the bio-signal comprises one of a heart rate and a breath rate of the target.

3. The processor implemented method of claim 2, wherein the predefined frequency range of the band pass filter for the heart rate is in a range of 0.9-3 Hz, and the predefined frequency range of the band pass filter for the breath rate is in a range of 0.2-0.9 Hz.

4. The processor implemented method of claim 1, wherein the in-phase baseband signal and the quadrature baseband signal are acquired using the sensor assembly located in a line-of-sight of the target, and wherein the sensor assembly comprises a first transducer for excitation of the target with the ultrasound signal and a second transducer for receiving a reflected signal from the target.

5. The processor implemented method of claim 1, wherein determining the value of the bio-signal is based on:

BR=int[$\alpha 1.BR_{Mag}$+(1−$\alpha 1$).$BR_{Ph}$] where 0<$\alpha 1$<1, when the bio-signal refers to a breath rate of the target $BR_{Mag}$ is the frequency of the most dominant peak in breaths per minute and is obtained by multiplying the frequency of the most dominant peak of the magnitude signal with 60, and $BR_{Ph}$ is the frequency of the most dominant peak in breaths per minute and is obtained by multiplying the frequency of the most dominant peak of the phase signal with 60.

6. The processor implemented method of claim 1, wherein determining the value of the bio-signal is based on the following equation when the bio-signal is heart rate of the target:

HR=int[$\alpha_2.HR_{mag}$+(1−$\alpha_2$).$HR_{Ph}$] where 0<$\alpha_2$<1

$HR_{Mag}$ is the frequency of the most dominant peak in breaths heart-beats per minute and is obtained by multiplying the frequency of the most dominant peak of the magnitude signal with 60, and $HR_{Ph}$ is the frequency of the most dominant peak in heart-beats per minute and is obtained by multiplying the frequency of the most dominant peak of the phase signal with 60.

7. A system for non-contact bio-sensing comprising:
one or more memories; and
one or more first hardware processors, the one or more first memories coupled to the one or more first hardware processors OW), wherein the one or more first hardware processors are configured to execute programmed instructions stored in the one or more first memories to:
  acquire an in-phase I(t) baseband signal and a quadrature Q(t) baseband signal associated with an ultrasound signal directed from a sensor assembly towards a target;
  calculate magnitude and phase signals from the in-phase I(t) and quadrature Q(t) baseband signals, wherein the magnitude and phase signals are obtained from the In-phase I(t) and the quadrature Q(t) baseband signals using the equations:

Magnitude, MAg=$\sqrt{I^2(t)+Q^2(t)}$

Phase, $\emptyset$=tan−1 (Q/I), wherein I channel is proportional to magnitude r(t) as I ∝A'/2 cos ($\emptyset$), and quadrature channel is 90 degrees out of phase with respect to an excitation signal v(t) as Q ∝A'/2 sin ($\emptyset$), wherein the phase $\emptyset$ is unwrapped as a chest wall movement x(t) of the target changes the phase response carrying intended information, wherein x(t)=$\alpha_b$ sin (2πf b t)+$\alpha_h$ sin (2πf h t) where, $\alpha_b$ and $\alpha_h$ is magnitude of the chest wall movement based on breathing and heart respectively, $f_b$ is breathing frequency, and $f_h$ is heart frequency;

filter the magnitude and phase signals by passing through a band pass filter associated with a predefined frequency range to obtain filtered magnitude and phase signals;
  identify, by performing Fast Fourier Transformation (FFT) of the filtered magnitude and phase signals, frequency of dominant peaks of spectrum of the magnitude and phase signals in the ultrasound signal; and
  determine value of a bio-signal associated with the target based on weighted values of the frequency of the dominant peaks of the magnitude and phase signals.

8. The system of claim 7, wherein the bio-signal comprises one of a heart rate and a breath rate of the target.

9. The system of claim 2, wherein the predefined frequency range of the band pass filter for the heart rate is in a range of 0.9-3 Hz, and the predefined frequency range of the band pass filter for the breath rate is in a range of 0.2-0.9 Hz.

10. The system of claim 7, wherein the in-phase baseband signal and the quadrature baseband signal are acquired using the sensor assembly located in a line-of-sight of the target, and wherein the sensor assembly comprises a first transducer for excitation of the target with the ultrasound signal and a second transducer for receiving a reflected signal from the target.

11. The system of claim 7, wherein the one or more hardware processors are configured by the instructions to determine the value of the bio-signal based on the following equation when the bio-signal is breath rate of the target:
BR=int[$\alpha 1.BR_{Mag}$+(1+$\alpha 1$).$BR_{Ph}$]
where 0<$\alpha 1$<1,
$BR_{Mag}$ is the frequency of the most dominant peak in breaths per minute and is obtained by multiplying the frequency of the most dominant peak of the magnitude signal with 60, and BRph $BR_{Ph}$ is the frequency of the most dominant peak in breaths per minute and is obtained by multiplying the frequency of the most dominant peak of the phase signal with 60.

12. The system of claim 7, wherein the one or more hardware processors are configured by the instructions to determine the value of the bio-signal based on the following equation when the bio-signal is heart rate of the target:

$$HR = int[\alpha_2 \cdot HR_{Mag} + (1-\alpha_2) \cdot HR_{Ph}] \text{ where } 0 < \alpha_2 < 1,$$

$HR_{Mag}$ is the frequency of the most dominant peak in breaths per minute and is obtained by multiplying the frequency of the most dominant peak of the magnitude signal with 60, and $HR_{Mag}$ is the frequency of the most dominant peak in heart-beats per minute and is obtained by multiplying the frequency of the most dominant peak of the phase signal with 60.

13. One or more non-transitory machine readable information storage mediums comprising one or more instructions which when executed by one or more hardware processors cause:

acquiring, via one or more hardware processors, an in-phase I(t) baseband signal and a quadrature Q(t) baseband signal associated with an ultrasound signal directed from a sensor assembly towards a target;

calculating, via the one or more hardware processors, magnitude, and phase signals from the in-phase I(t) and quadrature Q(t) baseband signals, wherein the magnitude and phase signals are obtained from the In-phase I(t) and the quadrature Q(t) baseband using the equations:

$$\text{Magnitude, Mag} = \sqrt{(I^2(t) + Q^2(t))}$$

Phase, $\emptyset = \tan{-1}(Q/I)$, wherein I channel is proportional to magnitude r(t) as $I \propto A'/2 \cos(\emptyset)$, and quadrature channel is 90 degrees out of phase with respect to an excitation signal v(t) as $Q \propto A'/2 \sin(\emptyset)$, wherein the phase $\emptyset$ is unwrapped as a chest wall movement x(t) of the target changes the phase response carrying intended information, wherein $x(t) = \alpha_b \sin(2\pi f_b t) + \alpha_h \sin(2\pi f_h t)$ where, $\alpha_b$ and $\alpha_h$ is magnitude of the chest wall movement based on breathing and heart respectively, $f_b$ is breathing frequency, and $f_h$ is heart frequency;

filtering, via the one or more hardware processors, the magnitude and phase signals by passing through a band pass filter associated with a predefined frequency range to obtain filtered magnitude and phase signals;

identifying, via the one or more hardware processors by performing Fast Fourier Transformation (FFT) of the filtered magnitude and phase signals, frequency of dominant peaks of spectrum of the magnitude and phase signals in the ultrasound signal; and determining, via the one or more hardware processors, value of a bio-signal associated with the target based on weighted values of the frequency of the dominant peaks of the magnitude and phase signals.

* * * * *